United States Patent [19]
Bertland et al.

[11] 4,317,811
[45] Mar. 2, 1982

[54] HERPES SIMPLEX TYPE 1 SUBUNIT VACCINE

[75] Inventors: Alexander U. Bertland, Lansdale; George P. Lampson, Hatfield, both of Pa.

[73] Assignee: Merck & Co., Inc., Rahway, N.J.

[21] Appl. No.: 186,365

[22] Filed: Sep. 11, 1980

[51] Int. Cl.³ ............................................ A61K 39/245
[52] U.S. Cl. ...................................... 424/89; 435/235; 435/239
[58] Field of Search ................... 424/89; 435/235, 239

[56] References Cited
FOREIGN PATENT DOCUMENTS 2140673 2/1972 Fed. Rep. of Germany .
2215728 10/1973 Fed. Rep. of Germany .
2848965 5/1980 Fed. Rep. of Germany .
53-04724 9/1978 Japan .

OTHER PUBLICATIONS

Tumilowicz et al. J. Med. Virol. (1978) 3(2): 151–156.
Zechel Eur. J. Biochem. (1977) 77(1): 133–139.
Denys, Med. Dosw. Mikrobiol. (1970) 22(3): 243–248.
Sitnikov et al. VOP. Virusol. (1968) 13(5): 554–560.
Farrah Canad J. Microbiol. (1979) 25(9): 145–151.
Powell et al. Nature 249, May 24, 1974: 360–361.
Kitces et al. Infection and Immunity Jun. 1977: 955–960.
C.A. 70:17,866e (1969).
C.A. 74:108,598t (1971).
C.A. 76:139,079v (1972).
C.A. 80:19,527a (1974).
C.A. 87:80,353b (1977).
C.A. 90:97,989y (1979).
C.A. 90:109,946x (1979).

Primary Examiner—Shep K. Rose
Attorney, Agent, or Firm—Donald J. Perrella; Hesna Pfeiffer

[57] ABSTRACT

A herpes simplex type 1 subunit vaccine is prepared from infected chick embryo cells by urea-extraction of the virus while the infected cells are still attached to the growth surface.

9 Claims, No Drawings

HERPES SIMPLEX TYPE 1 SUBUNIT VACCINE

BACKGROUND OF THE INVENTION

Field of the Invention

This invention relates to the preparation of a herpesvirus subunit vaccine, and in particular to a Herpes simplex type 1.

Herpesviruses are ubiquitous in nature; natural hosts include the frog, chicken, mouse, guinea pig, cat, dog, swine, cow, horse, monkey and man. Man is the natural host for Herpes simplex type 1 varicella/zoster, cytomegalovirus and Epstein-Barr. Clinical illness caused by herpes viruses presents a significant health problem for which no effective preventive measures are available. Herpes simplex type 1 (HSV1) is transmitted by the oral-respiratory route and is most frequently associated with oral lesions.

Members of the herpesvirus group are relatively large enveloped ether-sensitive DNA viruses. Herpes simplex type 1 viruses have been shown characteristically to contain two predominant molecular weight groups of envelope glycoproteins.

Herpesviruses present unique and individual problems for vaccine development, especially for use in man. Generally, viral vaccines, whether live attenuated vaccines or killed inactivated vaccines, are prepared from virus contained in animal host fluids or cell culture fluids or viral concentrates derived therefrom. However, herpesviruses in general tend to be more cell-associated than many other viruses, i.e., do not shed into the fluids, and, especially some members of the group, do not propagate readily to the high level of virions required for large scale manufacture of vaccine. Additionally, certain herpesviruses are suspected of being oncogenic for man. Preparation of vaccines from such viruses presents a special problem in that the vaccine must be free of any viral genetic information capable of inducing cancer. Even inactivated whole virus vaccines are viewed as potentially hazardous in such cases because they contain viral nucleic acid. Recently, efforts toward improved viral vaccines have lead to the development of subunit or "split" vaccines to reduce or remove unwanted host or viral components in the vaccines. An example in point is the preparation of influenza viral subunit vaccine from infected chick egg allantoic fluid to reduce the toxicity and pyrogenicity as described in U.S. Pat. No. 3,962,421. However, such subunit vaccines have not emphasized or demonstrated the removal and/or deactivation of viral genetic information as will be needed for viruses suspected of playing an etiologic role in cancer.

Objects of the Invention

It is an object of the present invention to provide a subunit antigen for a herpes simplex type 1 virus. Another object is to provide an immunogenic but non-pathogenic herpes simplex type 1 subunit antigen. A further object is to provide a herpes subunit antigen which can be used as a vaccine which protects a subject against the effects of this virus on both initial and subsequent challenge. Yet another object is to provide a method for effectively solubilizing and extracting non-pathogenic immunogenic antigens from virus-infected cells. Another object is to provide a method for concentrating these antigens and removing unwanted protein and nucleic acid. Another object is to provide compositions containing a herpes simplex type 1 subunit virus which are stable and storable. Still another object is to provide physiologically acceptable compositions for administering a herpes simplex type 1 subunit vaccine. These and other objects of the present invention will be apparent from the following description.

SUMMARY OF THE INVENTION

Primary chick embryo cells infected with HSV1 are prepared and subjected to the following sequence of operations to extract and concentrate the nonpathogenic, immunogenic antigens, separate them from unwanted materials, and treat them to render them satisfactory for use as a vaccine:

(1) the infected cells are extracted with urea while the cells are still attached to the growth surface, (2) the urea extract is purified, concentrated and inactivated, (3) the inactivated extract is treated to separate immunogenic fractions.

DETAILED DESCRIPTION

According to the present invention the starting material is herpes simplex virus type 1 (HSV1) infected cells propagated in cell culture. The cell may be any cell capable of being infected with the particular herpesvirus and of producing the desired viral antigens and considered acceptable for the preparation of a vaccine. For HSV1 vaccines for man, for example, a suitable cell culture system is primary chick embryo cells propagated as monolayers in roller bottles by procedures commonly used by those skilled in the art. The cells are infected with the HSV1 virus at a low multiplicity of infection (MOI, i.e., the number of virus particles per cell), such as an MOI of from about 0.001 to about 1.0, preferably about 0.01, by techniques commonly used by those skilled in the art and the cultures are incubated until viral cytopathogenic effect is observed in a large proportion of the cells, typically about 75% of the cells. At the end of the incubation period, the cell culture medium is removed and the cell monolayer is optionally washed with a salt solution, e.g., phosphate buffered saline (PBS).

HSV1 subunit antigens are then extracted directly from the cells attached to the growth surface by treating the cells with an aqueous urea solution, for example, a solution in PBS or water containing urea in concentration of at least about 2 M, at elevated temperature for up to several hours. The urea concentration may be from about 2 M to about 8 M, preferably about 4 M. The extraction preferably takes place with agitation. The elevated temperatures may be from about 30° C. to about 45° C. The extraction time may be from about 0.5 hour to about 5 hours. Either a single continuous or several successive extractions may be performed. Direct chemical extraction of the intact monolayer cell cultures offers a significant practical advantage for large scale vaccine manufacture as it does not require mechanical removal of the cells from the cell growth surface. It has also been found to give a higher protein yield by reducing physical losses involved in mechanical harvesting of cells. Under properly controlled conditions this procedure improves antigen purity by selective extraction of antigens.

The urea extract is then clarified, e.g. by centrifugation or filtration, and the supernatant liquid is then concentrated to reduce the volume of liquid. Preferably the volume is reduced to from 1/10 to 1/100 or more of the original volume. The concentrate is optionally but preferably homogenized and inactivated, e.g., by sonication or treatment with a detergent. Improved yields are obtained by heating the inactivated concentrate to from about 50° C. to about 75° C., e.g., by heating in a water bath.

The concentrate next is treated to remove DNA, e.g, by treating with an enzyme which degrades DNA, such as DNase to hydrolyze DNA, and fractionated chromatographically to separate immunogenic fractions. The immunogenic fractions are pooled and optionally but preferably homogenized and sterile filtered. The final product may be further treated by addition of formalin to a concentration of 90–100 μg/ml and by addition of thimerosal (1:20,000 vol/vol) to further insure against the presence of infectious viruses.

The herpes simplex type 1 immunogenic antigens of the present invention are immunogenic in mammalian species, e.g. mice, guinea pigs and baboons, and are useful as a vaccine to protect against herpes simplex type 1. The immunogenic antigens of the present invention may be administered by any convenient route, e.g. subcutaneously, intraperitoneally, or intramuscularly, in a dosage range of from about 0.1 to about 100 μg/dose preferably from about 5 to about 50 μg/dose, in order to obtain the desired immunogenic effect. The antigens may be administered in a single dose or in a plurality of doses at intervals of several weeks or more.

The immunogenic antigens of the present invention may be administered, if desired, in combination with vaccine stabilizers and vaccine adjuvants. Typically stabilizers are, for example, sucrose, an alkali metal hydrogen phosphate salt, glutamate, serum albumin, gelatin, or casein. The stabilizer may be any one or more of the foregoing. The adjuvant may be, for example, alum or a composition containing a vegetable oil, isomannide monooleate and aluminum monostearate. The immunogenic antigens of the present invention may be stored under refrigeration or in frozen or lyophilized form.

The following examples illustrate the present invention without, however, limiting the same thereto. All temperatures are expressed in degrees Celsius.

EXAMPLE 1

A cell sheet of chick embryo cells grown in roller bottles is infected on the fourth day after planting with herpes simplex type 1 virus. Six days post infection the cells are washed with 30 ml of PBS per liter bottle. The virus is extracted from the cells by treating the cells with 4 M urea in PBS for 75 minutes at 37° while rolling. The urea also may be made up in water. About 25 ml of the urea solution are used per liter bottle. The urea solution is sterilized prior to use by sterile filtering through a 0.22μ Millipore 293 mm filter. A second extraction under similar conditions is carried out and the two urea extracts are combined and clarified by centrifuging at 14,000 X g for 10 minutes with a continuous flow DeLaval centrifuge.

The supernatant liquid is concentrated 85-fold at room temperature on an Amicon Model TCID stack filter units, consisting of five 150 mm XM-100 filter pads. This concentrate is further concentrated to a 450-fold final concentration at room temperature on an Amicon Model 2000 stirred filter unit using an SM-100 Amicon filter 150 mm, at room temperature. After concentration, the filter is rinsed with 20 ml of eluate, which then is added to the concentrate. Next the concentrate is sonicated for 3 minutes at 60% of maximum power with a probe sonicator in ice bath, BIOSONIC II. The sonicated material is heated in a 60° water bath for three hours, then cooled to room temperature.

The concentrate then is treated with DNase at a concentration of 10 μg/ml+0.01 M $MgCl_2$ for 3 hours at room temperature and overnight at 4°. The DNase treated concentrate then is loaded on a 10 cm X 100 cm Pharmacia column packed with B10-gel A-5 M or Sephadex 6B-Cl and is gel chromatographed at room temperature. Fractionation is monitored by ultraviolet adsorption. The fractions at void volume are pooled and sonicated with a probe sonicator in ice bath. The sonicated material then is filtered through a 0.45μ Gelman filter of appropriate size, to obtain a sterile product which is stored at 4° C. The final product is sterility tested in thioglycolate medium, one ml product per 15 ml medium and incubated at 32° C. for 5 days.

The product is then examined for the presence of nucleic acid by a fluorometric method using ethidium bromide. Protein concentration of the product is determined by the Folin-Ciocalteau method. Carbohydrates are quantitatively determined by the phenolsulfuric acid method. Lipid content is identified after SDS polyacrylamide gel electrophoresis by staining with Sudan Black. SDS gel electrophoresis is also used for the determination of the number of minimum molecular weight peptides present in the final product by staining with Coomassie Blue. The product is further examined by rocket immunoelectrophoresis for the presence of chick cell protein, and quantitatively for any precipitating antigens. Electron microscopic record of the final product is made.

The product is optionally treated with formalin for 72 hours at 37° and with thimerosal (1:20,000). At the end of the formalin treatment excess formaldehyde is neutralized with $NaHSO_3$. A sterile suspension containing 30 ml PBS, 2 ml 10% $PO_4^=$ and 2.5 ml 10% alum is centrifuged at 3000 X G. The supernatant is decanted and 30 ml of product is added to the precipitate with stirring at room temperature for 2 hours. The adsorbed product is centrifuged in a clinical centrifuge. The supernatant liquid is removed and the precipitate is resuspended to the original volume with phosphate buffered saline. The amount of protein adsorbed is determined by the amount of protein left unadsorbed in the supernatant. The alum adsorbed product is stored at 4°.

EXAMPLE 2

Two groups of ICR/Ha mice, 20 mice per group, are injected intraperitoneally (i.p.) with two 0.5 ml injections on days 0 and 30 with either 0.5 ml of the alum adsorbed product of Example 1 or placebo. Each 0.5 ml dose of the alum adsorbed product of Example 1 contains 20 μg of HSV-1 subunit antigen. A third group of 5 mice receive no treatment. On day 44 the mice in all of the groups are challenged by infection with 0.5 ml of a $10^3$ dilution with HSV-1 (Schooler strain) i.p. and are monitored for survival for the next 21 days. Of the mice receiving the subunit antigen of Example 1, 19 (95%) are alive on day 65 while only 3 (15%) of the group receiving the placebo are alive. None of the group receiving no treatment is alive.

EXAMPLE 3

A group of 20 mice ranging in age from 3–12 weeks and ranging in weight from 20–35 g are injected intraperitoneally (i.p.) with two 0.5 ml doses of the alum-adsorbed product of Example 1 (20 μg/animal) at a one month interval. A second group of 20 mice receive a placebo and a third group of 37 mice receive no treatment. Two weeks after the last injection the mice are challenged with herpes simplex type 1, Schooler strain, (about $2 \times 10^5$ plaque forming units) by application to the abraded snout. Two mice from the placebo group die before challenge. Eighteen days post infection 17 mice (85%) are alive from the first group, and a combined total of 35 mice (64%) are alive from the 55 mice challenged from the placebo and no treatment groups.

What is claimed is:

1. A herpes simplex type 1 subunit vaccine prepared by the process comprising extracting cells infected with herpes simplex type 1 virus with urea while the cells are attached to the growth surface, clarifying the extract, concentrating the extract, and treating the extract to remove substantially all DNA.

2. A vaccine according to claim 1 wherein the urea has a concentration of from about 2 M to about 8 M.

3. A vaccine according to claim 1 wherein the urea extract is clarified by centrifugation or filtration.

4. A vaccine according to claim 1 wherein the clarified extract is concentrated by filtration.

5. A vaccine according to claim 1 wherein DNA is removed by treatment with an enzyme which degrades DNA.

6. A vaccine according to claim 5 wherein the enzyme is DNase.

7. A vaccine according to claim 1 wherein the extract after removal of DNA is gel chromatographed.

8. A vaccine according to claim 7 wherein the fractions at void volume are pooled and sterile filtered.

9. A vaccine according to claim 8 wherein the fractions are sonicated before filtering.

* * * * *